(12) United States Patent  (10) Patent No.: US 7,801,627 B2
Haldeman  (45) Date of Patent: Sep. 21, 2010

(54) CARDIAC LEAD HAVING SELF-EXPANDING FIXATION FEATURES

(75) Inventor: Paul C. Haldeman, Murrieta, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 213 days.

(21) Appl. No.: 11/957,943

(22) Filed: Dec. 17, 2007

(65) Prior Publication Data

US 2008/0097567 A1  Apr. 24, 2008

Related U.S. Application Data

(63) Continuation of application No. 11/113,667, filed on Apr. 25, 2005, now Pat. No. 7,330,765.

(51) Int. Cl.
*A61N 1/00* (2006.01)
(52) U.S. Cl. .................................................. 607/126
(58) Field of Classification Search .................. 607/50, 607/119, 122, 126; 600/124, 130, 143, 201, 600/372, 374–375, 508; 128/897, 898, 899; 623/1.18–1.2; 606/32, 41–50
See application file for complete search history.

(56) References Cited

U.S. PATENT DOCUMENTS

| | | | |
|---|---|---|---|
| 5,170,802 A | 12/1992 | Mehra | |
| 5,197,978 A * | 3/1993 | Hess | 623/1.18 |
| 5,221,261 A | 6/1993 | Termin et al. | |
| 5,224,491 A | 7/1993 | Mehra | |
| 5,449,372 A | 9/1995 | Schmaltz et al. | |
| 5,514,174 A | 5/1996 | Heil, Jr. et al. | |
| 5,531,779 A | 7/1996 | Dahl et al. | |
| 5,649,906 A | 7/1997 | Gory et al. | |
| 5,782,760 A * | 7/1998 | Schaer | 600/381 |
| 5,895,355 A * | 4/1999 | Schaer | 600/381 |
| 5,902,331 A | 5/1999 | Bonner et al. | |
| 5,954,761 A | 9/1999 | Machek et al. | |
| 6,136,021 A | 10/2000 | Tockman et al. | |
| 6,161,029 A | 12/2000 | Spreigl et al. | |
| 6,258,118 B1 * | 7/2001 | Baum et al. | 623/1.19 |
| 6,348,067 B1 * | 2/2002 | Baum et al. | 623/1.19 |
| 6,397,109 B1 | 5/2002 | Cammilli et al. | |
| 6,413,273 B1 * | 7/2002 | Baum et al. | 623/1.19 |
| 6,510,347 B2 | 1/2003 | Borkan | |
| 6,632,223 B1 * | 10/2003 | Keane | 606/41 |
| 6,709,415 B2 | 3/2004 | Navia | |
| 6,711,443 B2 | 3/2004 | Osypka | |
| 6,745,079 B2 | 6/2004 | King | |
| 6,842,648 B2 | 1/2005 | Partridge et al. | |
| 2002/0026228 A1 | 2/2002 | Schauerte | |
| 2002/0161427 A1 * | 10/2002 | Rabkin et al. | 623/1.11 |
| 2003/0204231 A1 | 10/2003 | Hine et al. | |
| 2004/0059404 A1 | 3/2004 | Bjorklund et al. | |
| 2005/0080472 A1 | 4/2005 | Atkinson et al. | |
| 2005/0203603 A1 | 9/2005 | Chitre et al. | |

* cited by examiner

*Primary Examiner*—Mark W Bockelman
*Assistant Examiner*—Elizabeth K So
(74) *Attorney, Agent, or Firm*—Faegre & Benson LLP (57) ABSTRACT

A cardiac lead for placement in the vicinity of a patient's heart is described. The lead includes a self-expanding fixation mechanism, which in a retracted position, is contained within a cavity disposed at a distal end of the lead. In an expanded position, the fixation mechanism extends axially from the distal end of the lead and expands radially into contact with a desired lumen site.

13 Claims, 10 Drawing Sheets

CARDIAC LEAD HAVING SELF-EXPANDING FIXATION FEATURES

CROSS-REFERENCE TO RELATED APPLICATION

This application is a continuation of U.S. patent application Ser. No. 11/113,667, filed Apr. 25, 2005, which is incorporated herein by reference in its entirety.

TECHNICAL FIELD

The present invention relates to implantable medical devices, in particular to cardiac leads and methods for delivering and affixing cardiac leads in a desired location in or near a patient's heart.

BACKGROUND

Cardiac function management systems are used to treat arrhythmias and other abnormal heart conditions. Such systems generally include cardiac leads, which are implanted in or about the heart, for delivering an electrical pulse to the cardiac muscle, for sensing electrical signals produced in the cardiac muscle, or for both delivering and sensing.

One difficulty with implanting leads in or about the heart is that the lead may become dislodged from its desired location during or after lead implantation. For example, the lead may become dislodged or otherwise repositioned when a clinician withdraws the guiding catheter used to initially implant the lead. Cardiac leads may also become dislodged by normal physiological activity. In an attempt to prevent cardiac leads from being dislodged, a variety of screws, anchors and other devices have been used to affix cardiac leads at a desired location at or near a patient's heart. Some of these devices, however, do not adequately affix the lead at the desired location. Other devices require a clinician to carry out complex, time-consuming steps during or after lead implantation to properly affix the lead at the desired location.

Accordingly, there is a need in the art for a cardiac lead having a fixation mechanism which effectively affixes the cardiac lead at a desired position without requiring complex steps during or after lead implantation.

SUMMARY

The present invention, according to one embodiment, is a cardiac lead including a conductive lead body having proximal and distal ends, a lead lumen and an actuator lumen, each lumen extending between the proximal and distal ends of the lead. The lead further includes an electrode coupled to the lead body and a self-expanding fixation mechanism coupled to the distal end of the lead, which has a retracted position in which the mechanism is substantially disposed within a cavity formed at the distal end of the lead, and an expanded position in which the mechanism extends distally from the distal end of the lead. The lead also includes an actuator which may be advanced through the actuator lumen disposed outside of the lead lumen to manipulate the fixation mechanism between the retracted and expanded positions.

According to another embodiment, the present invention is a cardiac lead including a conductive lead body having proximal and distal ends, a lead lumen extending between the proximal and distal ends for receiving a guiding member therein, and a cavity formed at the distal end of the lead. The lead lumen and cavity are in communication. The lead further includes an electrode coupled near the distal end of the lead body, and a self-expanding fixation mechanism as reported above, which further defines a channel such that a guiding member (e.g. stylet, guidewire, finishing wire) may extend through the lead lumen, the cavity and the fixation mechanism.

In yet another embodiment, the present invention is a cardiac lead including an electrode and means for fixing the distal end of the lead in the vicinity of the heart.

In a further embodiment, the present invention is a method of securing a cardiac lead within a body lumen. A cardiac lead is advanced to a desired lumen site within the patient. Then, the fixation mechanism reported herein may be deployed and allowed to expand into an expanded mode such that the expanded fixation mechanism contacts an inner wall of the body lumen. A conventional guiding catheter may be inserted prior to advancing the lead, and retracted after deploying the fixation mechanism. In the event that it become necessary or desirable to reposition the lead, the fixation mechanism can be returned back to the retracted position, the lead may be repositioned, and the fixation mechanism may be re-deployed. The fixation mechanism may also be utilized temporarily, and then retracted when the lead has become sufficiently fixed by tissue growth.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
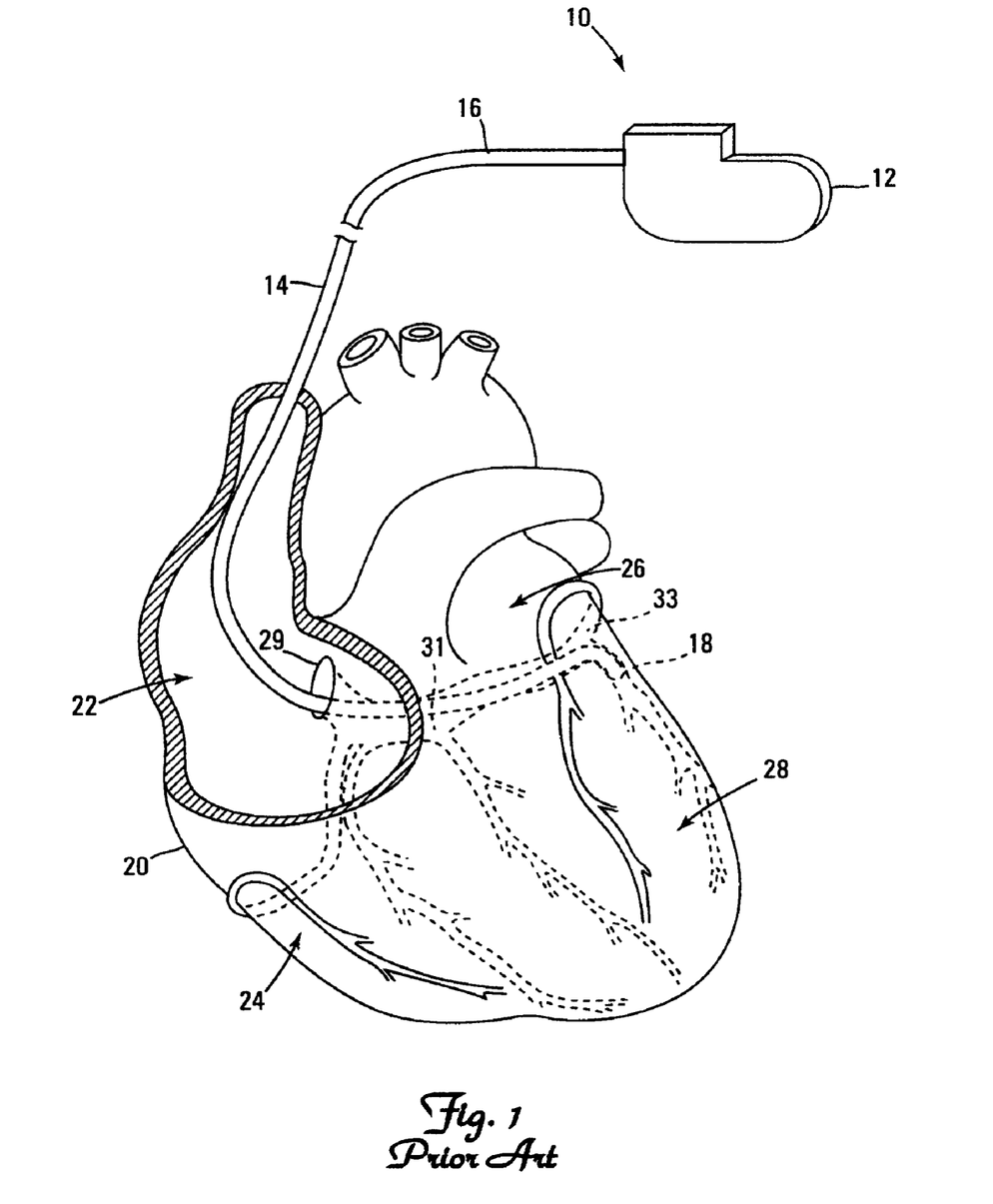
FIG. 1 is a schematic view of a cardiac lead implanted in a coronary vessel.

FIG. 1 is a schematic view of a cardiac rhythm management system 10 including a pulse generator 12 coupled to a lead 14 having a proximal end 16 and a distal end 18. As shown in FIG. 1, distal portions of the lead 14 are disposed in the patient's heart 20, which includes a right atrium 22, a right ventricle 24, a left atrium 26, and a left ventricle 28. In the embodiment illustrated in FIG. 1, the distal end 18 of the lead 14 is transvenously guided through the right atrium 22, through the coronary sinus ostium 29, and into a branch of the coronary sinus 31 or great cardiac vein 33. The illustrated position of the lead 14 may be used for sensing or for delivering pacing and/or defibrillation energy to the left side of the heart 20, to treat arrhythmias or other cardiac disorders requiring therapy delivered to the left side of the heart 20.

Figure 2A:
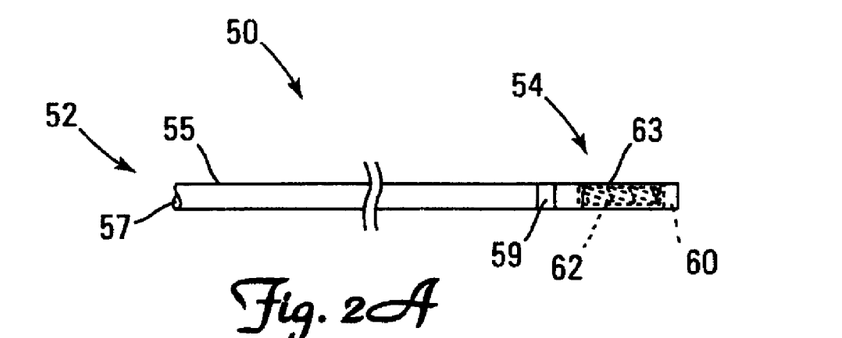
FIGS. 2A-2B show embodiments of the present invention in respective retracted and expanded positions.
Figure 2B:
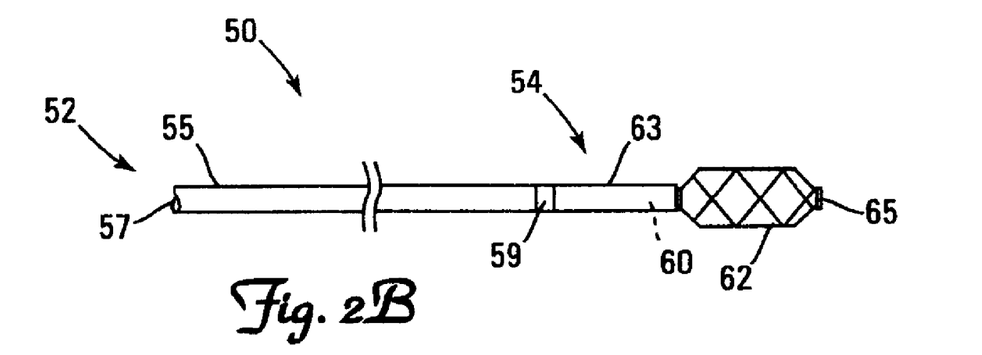

FIGS. 2A and 2B show schematic illustrations of distal portions of a cardiac lead 50 according to one embodiment of the present invention. As shown, the cardiac lead 50 includes a proximal end 52, a distal end 54, and a body 55 defining a lead lumen 57 extending between a proximal and distal ends 52, 54. The distal end 54 of the cardiac lead 50 may include one or more electrodes 59 that are in electrical communication with a conductive element (not shown) extending through the lead lumen 57. The cardiac lead 50, in one embodiment, has an outer diameter of from about 2 to about 10 French. In another embodiment, the outer diameter of the cardiac lead 50 is less than about 6 French.

As further shown in FIG. 2A, the distal end 54 of the lead 50 defines a cavity 60 which contains a self-expanding fixation mechanism 62. In FIG. 2A, the self-expanding fixation mechanism 62 is shown in a retracted position 63 inside of the cavity 60. In FIG. 2B the fixation mechanism 62 is shown in an expanded position 65 such that it extends distally from the distal end 54 of the lead 50 and radially to a diameter exceeding a diameter of the body 55.

As shown in FIGS. 2A-2B, the fixation mechanism 62 is self-expanding such that upon being deployed from the cavity 60, it automatically expands to the expanded position 65. As described in greater detail below, in the expanded position 65, the self-expanding fixation mechanism 62 fixes the lead 50 at a desired location in a body lumen such as, for example, a coronary vessel. In the embodiment illustrated in FIGS. 2A-B, the self-expanding fixation mechanism 62 resembles a stent similar to the stents employed in vascular intervention procedures, except that the stent is crimped down at a proximal end and also at a distal end.

The fixation mechanism 62 may be formed from a variety of suitable self-expanding materials. Suitable self-expanding materials generally have shape-memory properties, and have sufficient resiliency to expand upon deployment. Suitable materials may include stainless steel as well as a variety of alloys and polymers. The fixation mechanism 62 may be constructed from any superelastic material that allows it to self-expand upon deployment from the cavity 60. Such self-expanding materials are well known in the art. In one embodiment, for example, the fixation mechanism 62 is made at least partially from nitinol. Additionally, in certain embodiments, the fixation mechanism 62 may also function as an electrode. In these embodiments, a conductive element (not shown) would extend through the cardiac lead 50 and would be electrically coupled to the fixation mechanism 62.

Figure 3:
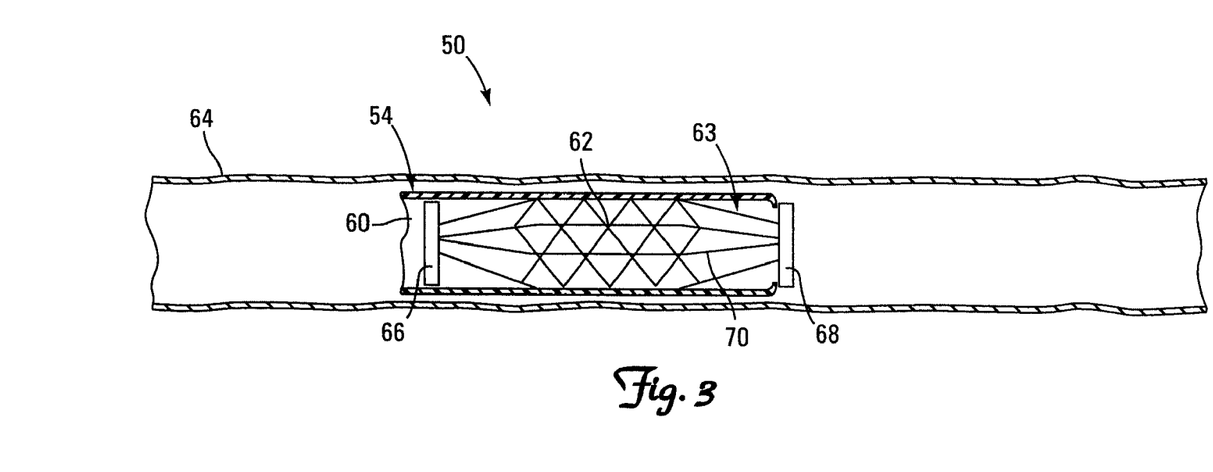
FIG. 3 shows a cross-sectional view of an embodiment of the present invention in a retracted position within a vessel.

FIG. 3 is a cross-sectional view of a body lumen 64 such as, for example, a coronary vessel into which the lead 50 has been advanced. In FIG. 3, the fixation mechanism 62 is retained in the retracted position 63 by a wall defining the cavity 60. The fixation mechanism 62 includes a proximal base 66, a distal base 68, and a plurality of interconnected stent tines 70 extending between the proximal and distal bases 66, 68.

Figure 4:
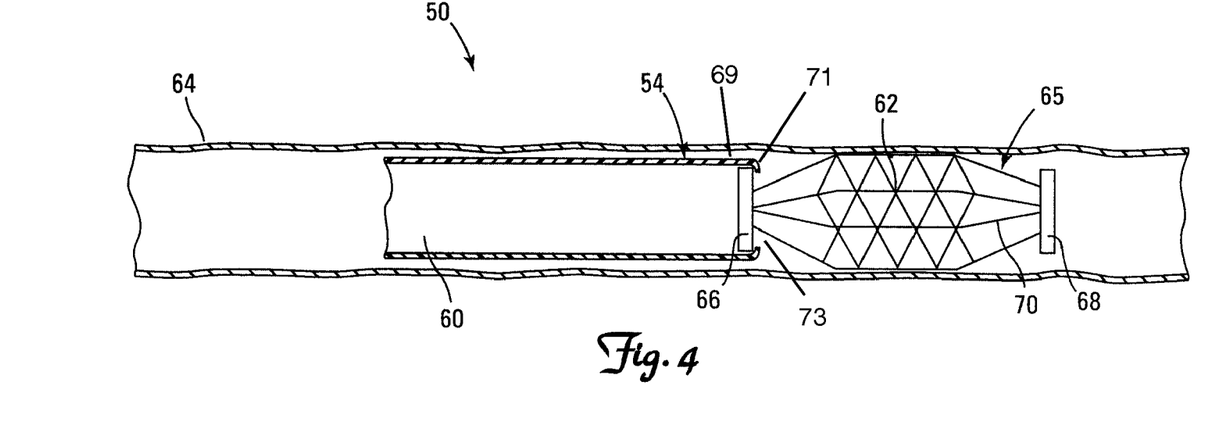
FIG. 4 shows a cross-sectional view of the embodiment shown in FIG. 3 in an expanded position within a vessel.

FIG. 4 is a cross-sectional view of the distal end 54 of the lead 50 shown in FIG. 3, in which the fixation mechanism 62 is in the expanded position 65. In the expanded position 65, the distal base 68 and stent tines 70 extend distally relative to the cavity 60, and the fixation mechanism 64 contacts the body lumen 64 with sufficient radial force to adequately secure the cardiac lead 50 to the body lumen 64. The proximal base 66 is retained within the cavity 60 by a tapered portion 69 at the opening of the cavity 60 so that the fixation mechanism 62 remains associated with the distal end 54 of the lead 50. In some embodiments, the tapered portion 69 includes a lip 71 defining an opening 73.

In one embodiment of the present invention, the cardiac lead 50 is configured such that conventional lead implantation procedures may be utilized while still allowing for the actuation of the fixation mechanism 62. More particularly, the lead 50 may be configured to allow the passage of a guiding member such as a guidewire or stylet through the lead lumen, without interfering with the deployment and/or retraction of the fixation mechanism 62.

Figure 5A:
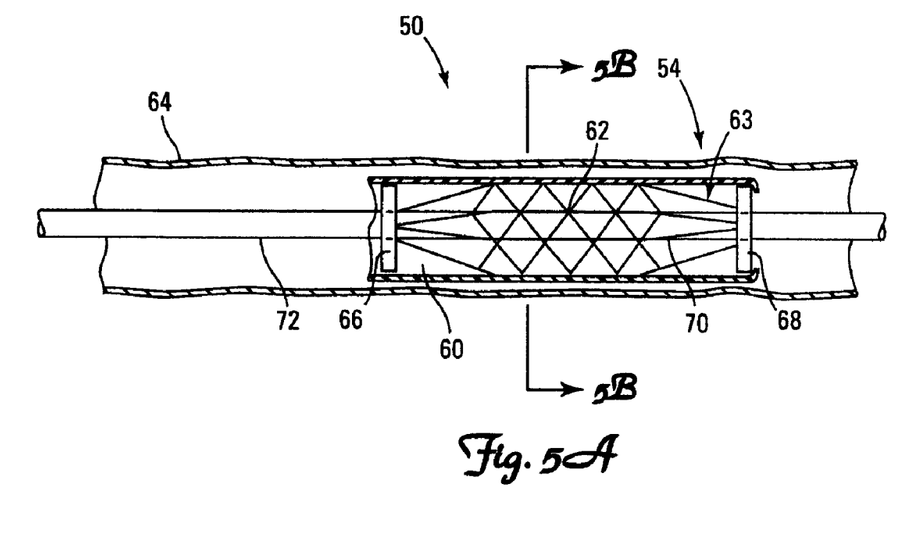
FIGS. 5A-5B show cross-sectional views of an embodiment of the present invention in a retracted position within a vessel.
Figure 5B:
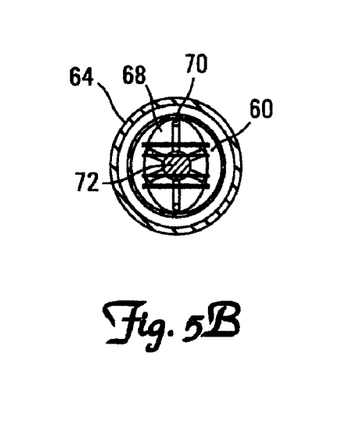

In FIGS. 5A-5B, for example, the cavity 60 is in communication with the lead lumen 57 (See FIGS. 2A-2B) via an opening (not shown) between the lead lumen 57 and the cavity 60, which allows the passage of a guiding member 72. As further shown in FIG. 5B, the fixation mechanism 62 defines a channel extending through the proximal and distal bases 66, 68 and the tines 70, through which the guiding member 72 may pass during lead implantation. In this manner, the lead 50 may be implanted using a guiding member 72 (e.g., a guidewire or stylet) which extends past the distal end of the fixation mechanism 62.

In an alternate embodiment, the cardiac lead 50 may be configured such that the cavity 60 and the lead lumen 57 are not in communication. For example, in the embodiment shown in the cross-sectional illustration of FIG. 6, the lead body 55 (see FIGS. 2A-2B) may include first and second lumens 80, 82. The first lumen 80 is adapted to receive the guiding member 72 and may optionally include a distal opening disposed proximally to the fixation mechanism 62 for receiving a guiding member 72 such as a guidewire.

Figure 6:
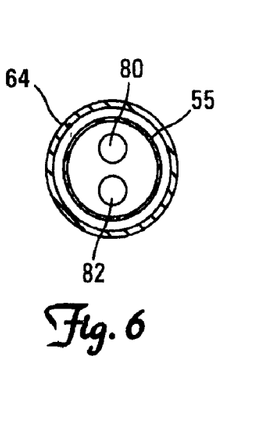
FIG. 6 shows a cross-sectional view of an embodiment of the present invention within a vessel.

The second lumen 82 is in communication with the cavity 60, and may be used to facilitate deployment of the fixation mechanism 62 as described in further detail below. Although the first and second lumens 80, 82 are shown as being substantially parallel, other configurations may be suitable for embodiments of the present invention. For example, the first and second lumens may extend concentrically through the lead 50 and diverge near the distal end 54 of the lead 50. Alternatively, a single lumen 57 could extend through the lead 50 and diverge into two discrete branches 80, 82 near the distal end 54 of the lead 50.

Figure 7:
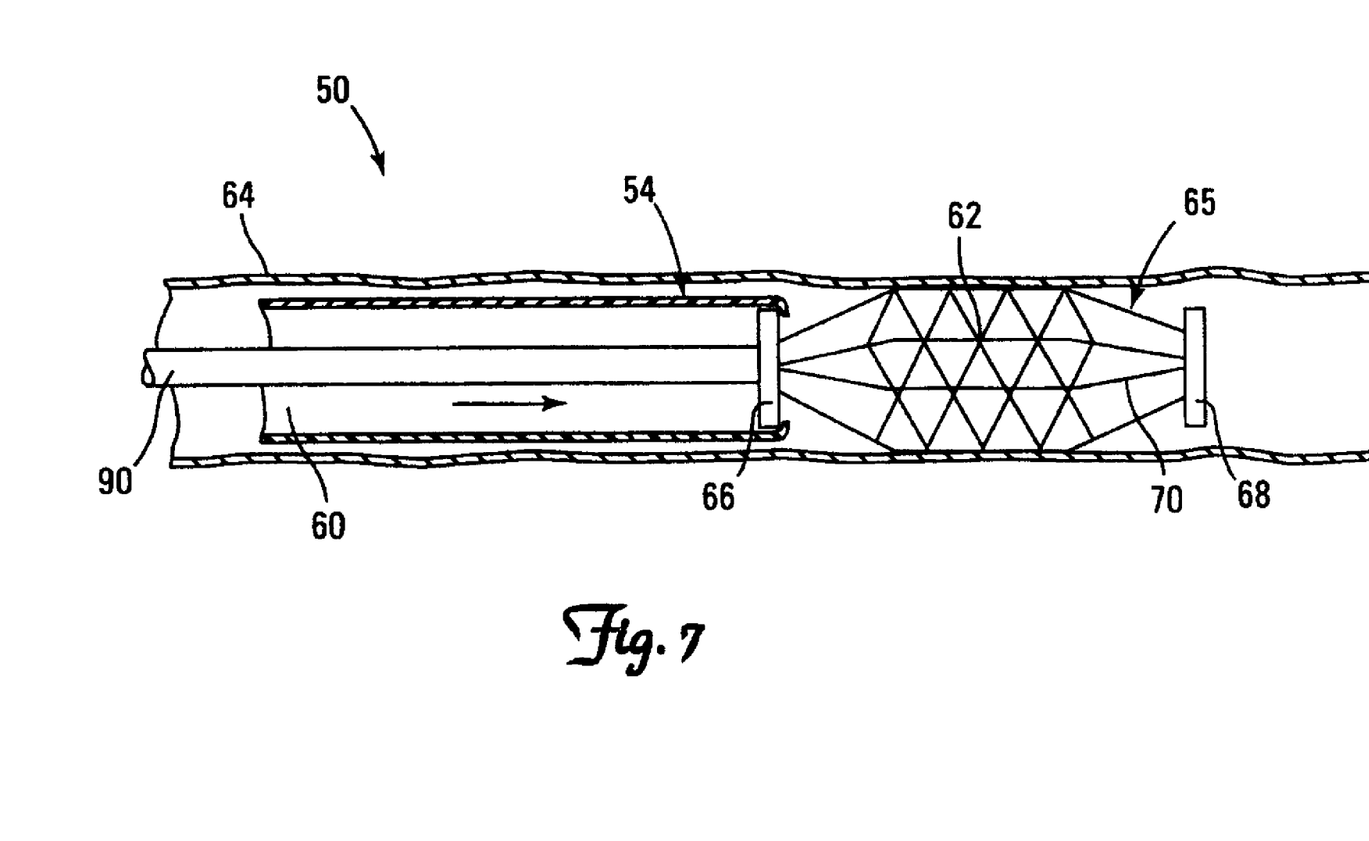
FIG. 7 shows a cross-sectional view of an embodiment of the present invention in an expanded position within a vessel.

A variety of approaches may be used to deploy and/or retract the fixation mechanism 62 depending on the configuration of the lead 50. In the embodiment shown in FIG. 7 in which the lead lumen is in communication with the cavity 60, a stylet 90 or similar device may be inserted through the lead lumen and into the cavity 60 until it contacts the proximal base 66. Corresponding structure between the stylet 90 and the base 66 may be utilized to facilitate actuation of the fixation mechanism 62 between extended and retracted positions.

Figure 8:
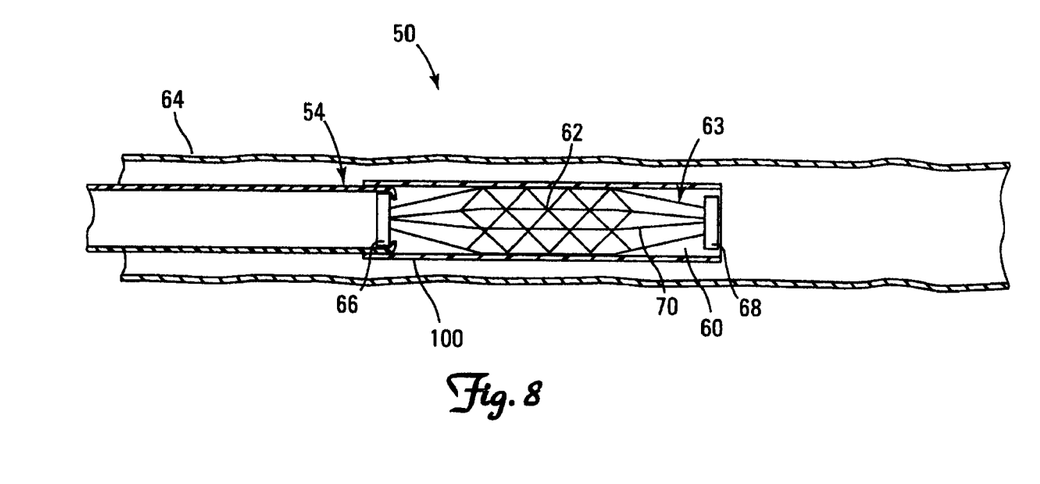
FIG. 8 shows a cross-sectional view of an embodiment of the present invention in a retracted position within a vessel.
Figure 9:
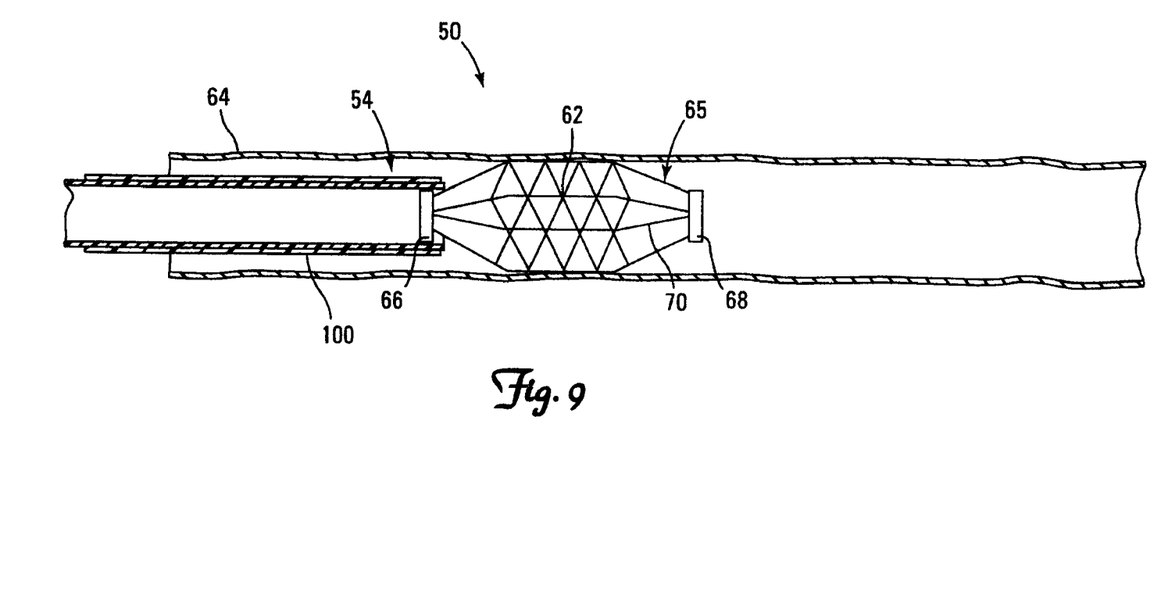
FIG. 9 shows a cross-sectional view of the embodiment shown in FIG. 8 in an expanded position within a vessel.

In a further embodiment shown in FIGS. 8-9, the cavity 60 is defined by a sheath 100 that extends from a distal end 54 of the lead device 50. The sheath 100 operates in one of at least two ways. First, as shown in FIGS. 8-9, the sheath 100 may be actuated relative to the fixation mechanism 62 such that the fixation mechanism is deployed when the sheath 100 is actuated. For example, the sheath 100 may be configured such that the application of a force in the direction of the proximal end of the lead device 50 results in retraction of the sheath 100 over the distal end 54 of the lead 50, which deploys the fixation mechanism 62 into the expanded mode 65. In this embodiment, the fixation mechanism 62 remains in a fixed axial position relative to the distal end 54 of the lead, and the movement of the sheath 100 dictates whether the fixation mechanism 62 is in the retracted 63 or expanded position 65. In an alternate embodiment, the sheath 100 may be retracted into the distal end 54 of the lead 50.

In embodiments in which the cavity 60 is defined by a movable sheath 100, an actuator such as a stylet wire 90 may be configured to retract the sheath 100 proximally to deploy the fixation mechanism 62. Alternatively, the sheath 100 may remain fixed relative to the distal end 54 of the cardiac lead 50. In this embodiment, the fixation mechanism 62 moves relative to the sheath 76 to provide the retracted or compressed position 63 and the expanded position 65. In one embodiment, the cardiac lead 50 includes an actuator coupled to the sheath 100, which operates to both retract the sheath 100 to allow the fixation mechanism 62 to assume the expanded position 65 and advance the sheath 100 to return the fixation mechanism 62 to the compressed position 63.

The sheath 100 may be formed from a range of biocompatible materials having sufficient strength to retain the fixation mechanism 62 in a compressed mode 63. For example, the sheath 100 may be formed from a wide variety of suitable biocompatible polymeric materials such as medical grade silicone or polyurethane.

Figure 10A:
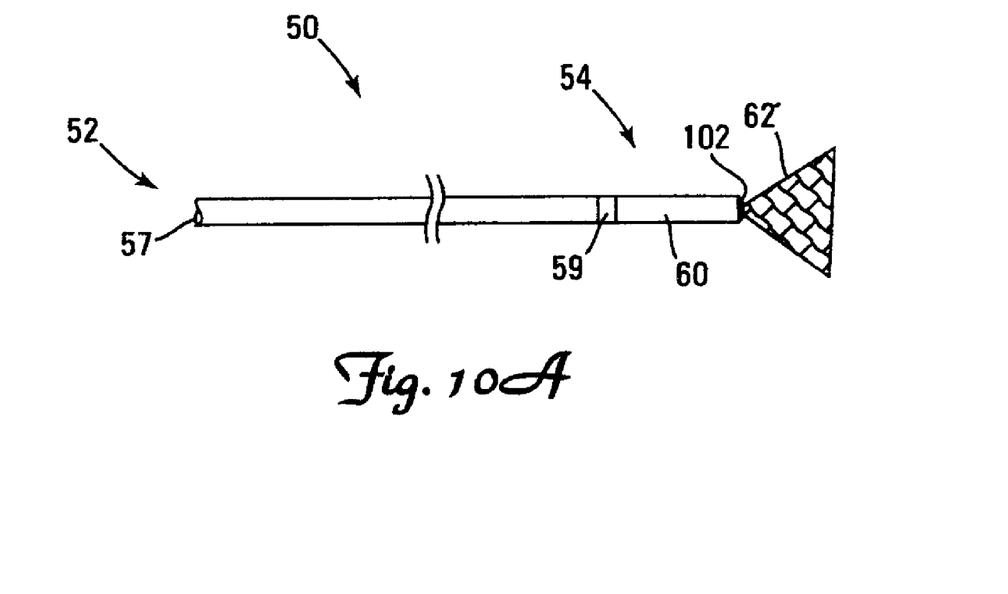
FIGS. 10A-10B show alternate embodiments of the present invention.
Figure 10B:
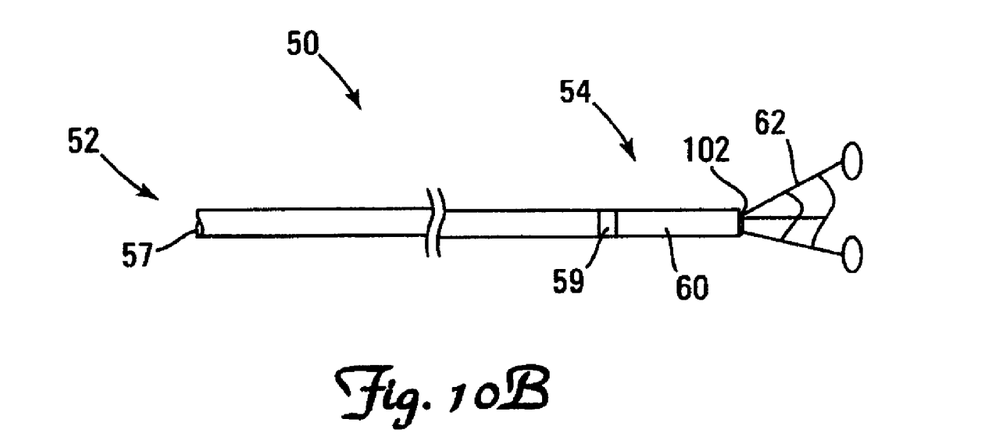

As shown in FIGS. 10A-10B and 11A-11D, the fixation mechanism 62 may be formed in a variety of configurations in addition to the stent-like configuration previously described. In FIGS. 10A-10B, the fixation mechanism 62 includes a plurality of interconnected tines to form, for example, a net-like structure (FIG. 10A) or a web-like structure (FIG. 10B).

Figure 11A:
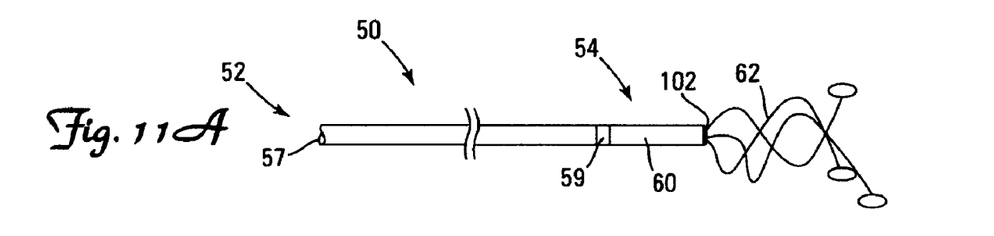
FIGS. 11A-11E show further embodiments of the present invention.
Figure 11B:
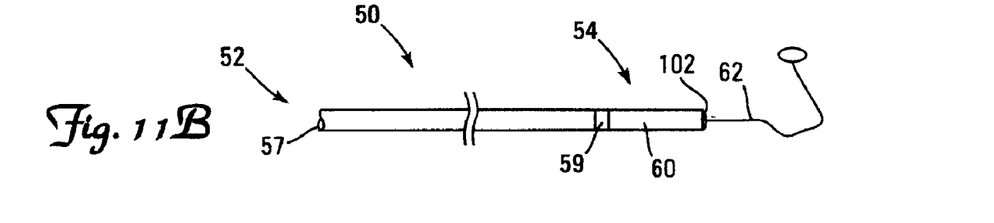
Figure 11C:
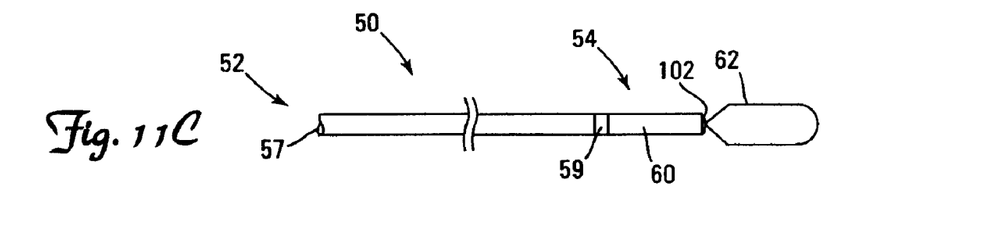
Figure 11D:
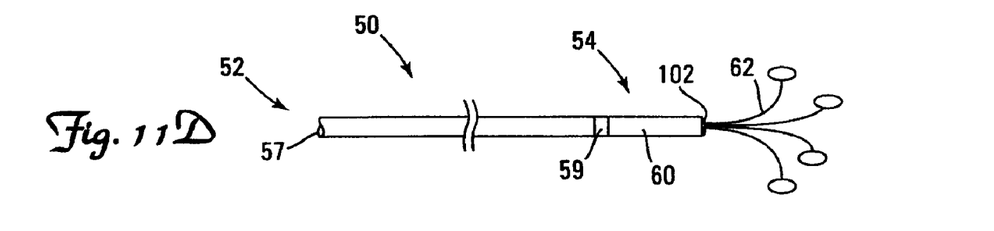
Figure 11E:
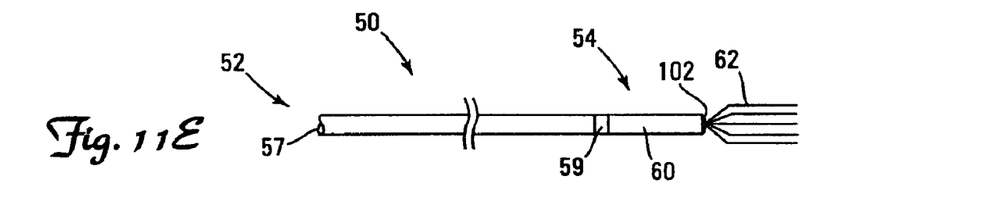

In FIGS. 11A-11D, the fixation mechanism 62 is configured with one or more discrete tines, for example, one or more sinusoidal tines (FIG. 11A), one or more hook tines (FIG. 11B), one or more loop tines (FIG. 11C), one or more leaf tines (FIG. 11D) or one or more finger tines (FIG. 11(e). In the illustrated embodiments, the tines are secured by a base 102, which remains at least partially disposed within the cavity 60. The structure of the fixation mechanism 62 is self-expanding after deployment from the cavity 60, is sized and shaped to fix the distal end 54 of the cardiac lead 50 at the desired lumen location, and is configured to provide for conventional implantation of the lead 50.

The lead 50 and the fixation mechanism 62 may be dimensioned to provide for optimal fixation without disturbing lead implantation or functionality. In one embodiment, the lead 50 has a diameter of less than about 6 French. In this embodiment, the fixation mechanism 62 may be configured to have a major dimension (e.g. diameter) less that the diameter of the lead 50 when in a retracted position, and greater than the diameter of the lead in an expanded position in order to contact the vessel wall.

Figure 12:
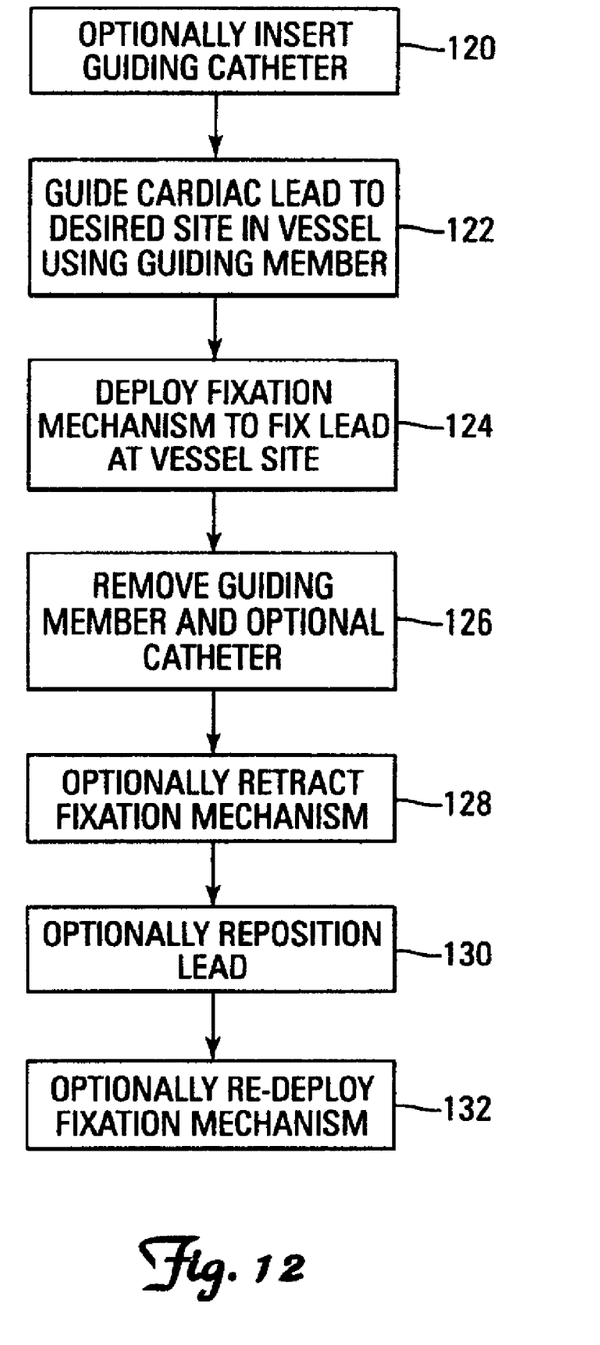
FIG. 12 is a flowchart illustrating one method of using embodiments of the present invention.

FIG. 12 shows a method of implanting the lead 50 according to an embodiment of the present invention. Initially, one or more guiding catheters may be optionally guided into a desired vessel (block 120). The cardiac lead 50, which is configured such that the fixation mechanism 62 is in the compressed mode 63, may then be guided through the guiding catheter(s) to a desired vessel site (block 122). After positioning the distal end 54 of the lead at the desired site, the fixation mechanism 62 may then be deployed into the expanded mode 65 to contact an inner surface of the patient's lumen and to affix the distal end 54 of the lead device 50 at the desired site (block 124). After fixation, the guiding catheter and guide member may be removed without dislodging the distal end 54 of the lead device 50 (block 126).

After removal of the guiding catheter and/or guide member, the fixation mechanism 62 may be retracted or remain permanently fixed. Likewise, if a clinician desires to the reposition the lead, the fixation device 62 may be retracted into the cavity 60 to allow the lead to be repositioned (blocks 128 and 130). The fixation mechanism 62 may then be re-deployed (block 132). Additionally, after sufficient tissue in-growth has occurred, it may be desirable to retract the fixation mechanism 62 permanently. However, the fixation mechanism 62 is capable of substantially permanent deployment to prevent the lead device 50 from becoming dislodged or otherwise repositioned during use.

Figure 13:
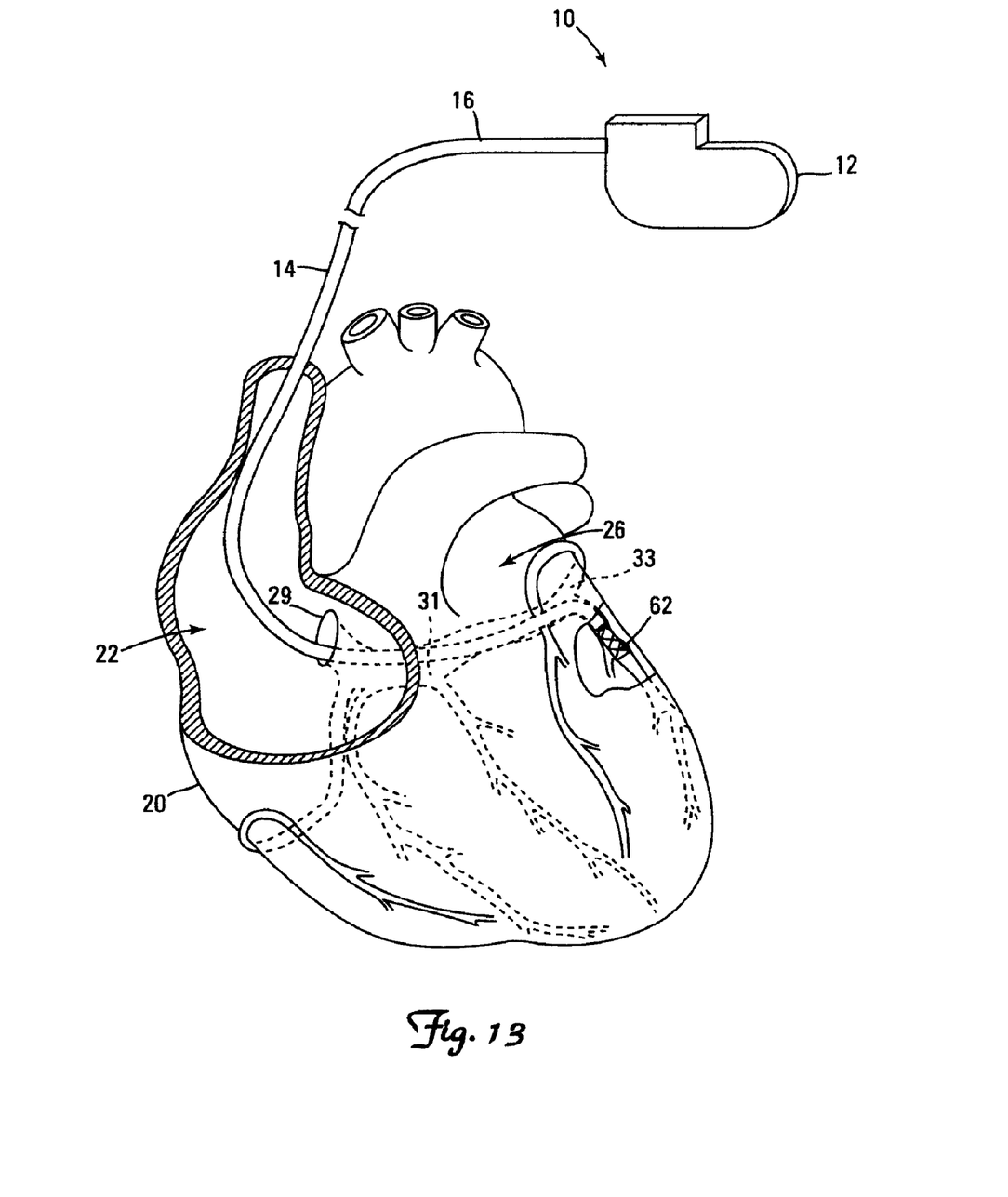
FIG. 13 shows an embodiment of the present invention implanted in a coronary vessel.

FIG. 13 is a schematic view of a cardiac rhythm management system 10, showing a cardiac lead 50 secured within a coronary vessel, according to one embodiment of the present invention. As shown in FIG. 13, the fixation mechanism 62 has been deployed and has radially-expanded to contact an inner surface of the vessel wall.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

I claim:

1. A cardiac lead comprising:
   a lead body including a conductor, the lead body extending from a proximal end configured to be connected to a pulse generator to a distal end defining a cavity including a circumferential lip defining a constricted opening having a reduced diameter less than an inner diameter of the lead body and a guide lumen extending from the proximal end to the distal end;
   an electrode operatively coupled to the conductor;
   a fixation mechanism configured to facilitate extension of a guiding member beyond the distal end of the lead body, the fixation mechanism comprising: a base disposed within the cavity, the base having an outer diameter greater than the reduced diameter of the constricted opening such that the circumferential lip is configured to engage and retain the base within the cavity; one or more expandable tines having a proximal end coupled to the base and extending in a distal direction away from the base, and a channel defined in and extending through the base, the channel facilitating extension of the guiding member beyond the distal end of the lead body, wherein the fixation mechanism is adapted to transition from an expanded position beyond the distal end of the lead body, to a retracted position located within the cavity, wherein when the fixation mechanism is in the expanded position, the base is engaged by the circumferential lip of the cavity such that the base is retained within the cavity at the distal end of the lead body and the one or more expandable tines extend in a distal direction away from the distal end of the lead body and the fixation mechanism remains associated within the distal end of the lead body; and a guiding member adapted to extend beyond the distal end of the lead body.

2. The cardiac lead according to claim 1, further comprising an actuator mechanism operable to manipulate the fixation mechanism from the expanded configuration to the retracted configuration.

3. The cardiac lead of claim 1, wherein in the retracted configuration, the fixation mechanism is substantially disposed within the cavity and wherein in the expanded position, the fixation mechanism extends distally from the distal end of the lead body.

4. The cardiac lead of claim 1, wherein the fixation mechanism comprises one or more discrete tines having a sinusoidal, loop, hook, leaf, or finger configuration.

5. The cardiac lead of claim 1, wherein the fixation mechanism includes one or more tines comprising a shape memory material.

6. The cardiac lead according to claim 1, further comprising an actuator operable to move the fixation mechanism longitudinally from the expanded configuration to the retracted configuration.

7. The cardiac lead according to claim 1, wherein the actuator is connected to the fixation mechanism.

8. The cardiac lead according to claim 1, wherein the actuator comprises a stylet.

9. The cardiac lead according to claim 1, wherein the guiding member comprises a guidewire.

10. The cardiac lead according to claim 1, further comprising an actuator lumen for an actuator, the actuator lumen extending from the proximal end to the distal end.

11. A method of implanting a cardiac lead comprising:

guiding a cardiac lead over a guiding member to a desired vessel site, the cardiac lead comprising a lead body including a conductor extending from a proximal end configured to be connected to a pulse generator to a distal end defining a cavity including a circumferential lip defining a constricted opening having a reduced diameter less than an inner diameter of the lead body, a guide lumen extending from the proximal end to the distal end, an electrode operatively coupled to the conductor; and a fixation mechanism adapted to transition from an expanded configuration in which the fixation member extends in a distal direction away from the distal end of the lead body to a retracted configuration in which the fixation mechanism is retained within the cavity; the fixation mechanism configured to facilitate extension of the guiding member beyond the distal end of the lead body, the fixation mechanism comprising a base disposed within the cavity, the base having an outer diameter greater than the reduced diameter of the constricted opening such that the circumferential lip is configured to engage and retain the base within the cavity when the fixation mechanism is in the expanded position so that the fixation mechanism remains associated within the distal end of the lead body, one or more expandable tines coupled at a proximal end to the base and extending in a distal direction away from the base, and a channel defined in and extending through the base, the channel facilitating extension of the guiding member beyond the distal end of the lead body;

positioning the distal end of the lead body at the desired vessel site;

deploying the fixation mechanism such that the fixation mechanism transitions from the retracted configuration in which the fixation mechanism is disposed within the cavity defined by the distal end of the lead body to the expanded configuration in which the fixation mechanism extends beyond the distal end of the lead body, wherein when the fixation mechanism is in the expanded position the base is engaged by the circumferential lip such that the base is retained within the cavity at the distal end of the lead body and the one or more expandable tines extend in a distal direction away from the distal end of the lead body; and transitioning the fixation mechanism from the expanded configuration to the retracted configuration.

12. The method according to claim 11, further comprising repositioning the distal end of the lead body.

13. The method of claim 12, wherein the step of repositioning the distal end of the lead body further comprises re-deploying the fixation mechanism such that the fixation mechanism transitions from the retracted configuration to the expanded configuration.

* * * * *